United States Patent [19]

Hojaiban

[11] 4,018,219
[45] Apr. 19, 1977

[54] HEART RATE VARIABILITY MEASUREMENT

[75] Inventor: George Hojaiban, Newington, Conn.

[73] Assignee: American Home Products Corporation, New York, N.Y.

[22] Filed: Nov. 3, 1975

[21] Appl. No.: 628,084

[52] U.S. Cl. .................................... 128/2.06 A
[51] Int. Cl.² ................................... A61B 5/04
[58] Field of Search ............. 128/2.05 P, 2.05 R, 128/2.05 T, 2.06 A, 2.06 F, 2.06 R

[56] References Cited

UNITED STATES PATENTS

| | | | |
|---|---|---|---|
| 3,524,442 | 8/1970 | Horth | 128/2.06 A |
| 3,599,628 | 8/1971 | Abbenante et al. | 128/2.06 F |
| 3,633,569 | 1/1972 | Brayshaw et al. | 128/2.06 A |
| 3,699,949 | 10/1972 | O'Hanlow, Jr. et al. | 128/2.06 A |
| 3,861,387 | 1/1975 | Lawhorn et al. | 128/2.06 A |
| 3,878,833 | 4/1975 | Arneson et al. | 128/2.06 A |
| 3,880,147 | 4/1975 | Gruenke et al. | 128/2.06 F |

*Primary Examiner*—William E. Kamm
*Attorney, Agent, or Firm*—Darby & Darby

[57] ABSTRACT

A method and apparatus for quantitative measurement of the long-term and short-term variability of a subject's heart rate. Long-term variability is measured by apparatus which receives a signal having a magnitude proportional to a subject's instantaneous heart rate with each successive heart beat during a measuring interval consisting of a fixed number of heartbeats. Each heart rate signal magnitude is compared with the previous maximum and minimum heart rate signal magnitudes in the measuring interval and the sampled heart rate magnitude is substituted for the previous maximum signal magnitude if the maximum is exceeded and for the previous minimum signal magnitude if it exceeds the magnitude of the instant sampled heart rate signal. The difference between the maximum and minimum heart rate signal magnitudes, after occurrence of the predetermined number of heartbeats, is a measure of long-term heart rate variability. To measure short-term variability the apparatus determines the average of the differences in time between successive heart beats for the predetermined number of heartbeats by comparing each latest time difference with the previous time difference and incrementing or decrementing the previous time difference until it equals the latest time difference. The number of increments or decrements are counted and divided by the predetermined number of heartbeats comprising the measuring interval to yield a measure of short-term variability.

15 Claims, 7 Drawing Figures

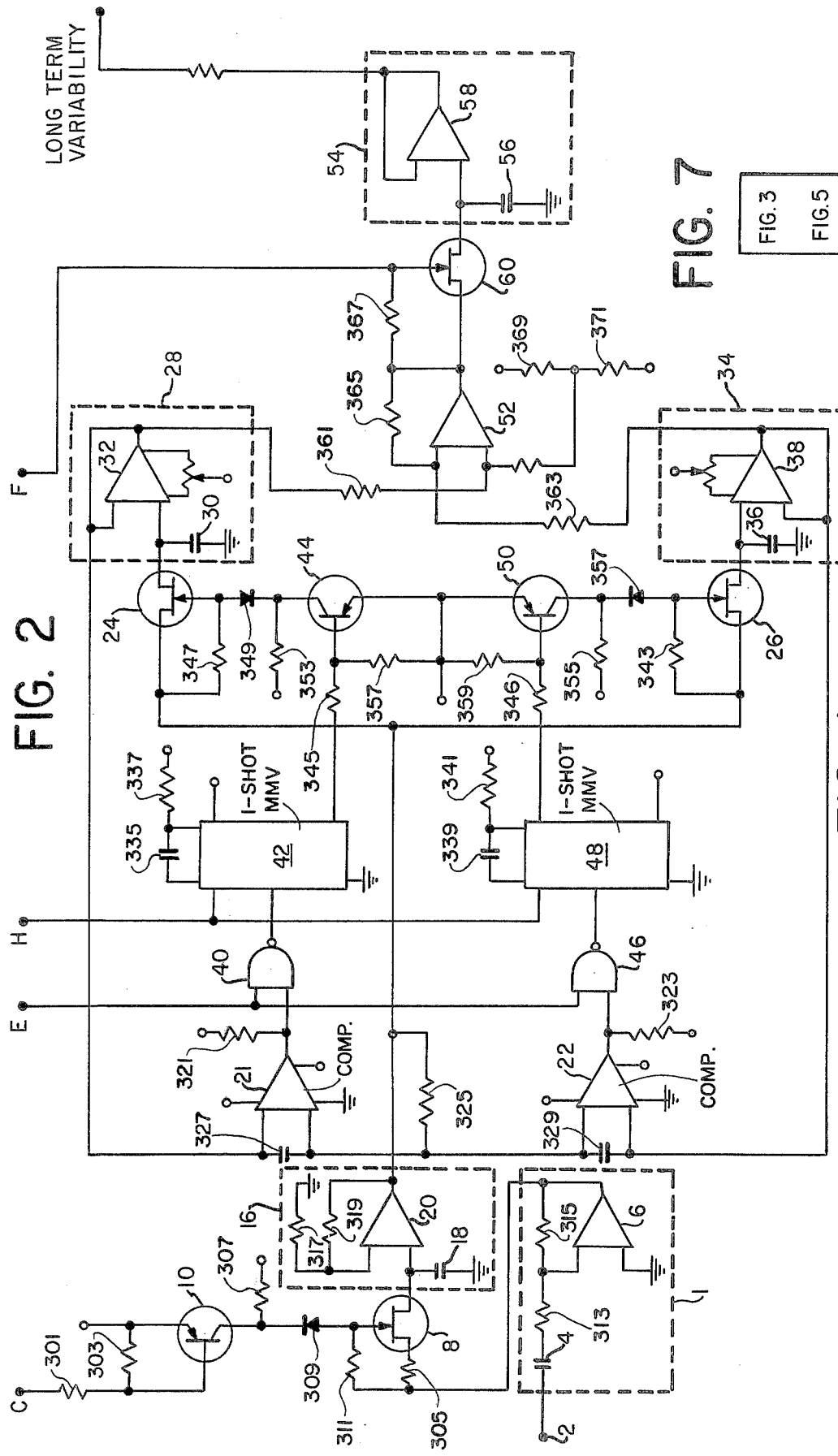

HEART RATE VARIABILITY MEASUREMENT

BACKGROUND OF THE INVENTION

It is known that the heart rate of a healthy human varies over time within maximum and minimum heart rate limits. Absence of or diminution in heart rate variability has been found to be a useful indicator of fetal distress and apparatus has been developed to monitor fetal heart rate variability and alert medical personnel when variability is insufficient. Such a system constitutes the subject matter of application Ser. No. 571,380 filed on Apr. 24, 1975 in the name of George Hojaiban and assigned to the assignee of this invention. It has been found that the usefulness of the variability parameter is not limited to fetal monitoring and its measurement is at least equally beneficial in the case of neonatal monitoring.

Since a newborn is unable to communicate symptoms of illness, its bodily functions must be monitored by some external means in order for its condition to be determined. It is desirable to obtain a quantitative measurement of heart rate variability so that the degree of severity of condition of the neonate may be known. Furthermore, since the range of acceptable values of heart rate variability may differ from one neonate to another, depending upon size, weight, physiology, sex, and other characteristics, it is additionally desirable to have a capability for assigning tolerance limits for normal variability to each specific subject. Physicians may differ in their judgment as to what constitutes normal variability and when programming an alert system to sound an alarm for abnormal variability, it is desirable to permit the physician to preselect specific tolerance limits geared to the specific patient. Prior art variability monitors have only been able to determine whether variability is acceptable or unacceptable by qualitative measurement and to measure the period of time over which an acceptable or unacceptable condition exists in order to alert for variability.

SUMMARY OF THE INVENTION

The shortcomings of the prior art qualitative variability evaluation systems are overcome by the instant invention which permits a continuous quantitive determination of heart rate variability. More specifically, the instant invention provides direct numerical measurement of (a) long-term and short-term heart rate variability in beats per unit time and (b) time between beats which measurements may be recorded or displayed to inform medical personnel of the condition of a neonate or other subject. Both heart rate units (beats per minute) and time units (milliseconds between heart beats) may be used to measure long-term and short-term variability.

An electrical signal indicative of a subject's heart rate measured with each heartbeat is applied to the apparatus of the invention. In order to measure long-term variability, a voltage proportional to the instantaneous heart rate is compared with voltages proportional to the maximum and minimum values of the previously measured heart rates to determine whether a new maximum or minimum has been reached. If so, the previous maximum or minimum heart rate voltage is replaced with a voltage proportional to the new maximum or minimum heart rate as the case may be. Each newly sampled heart rate voltage is compared with the maximum and minimum heart rate voltage for a predetermined number of heartbeats after which time the minimum heart rate voltage is subtracted from the maximum heart rate voltage to form a difference voltage which represents a numerical measurement of long-term heart rate variability.

For short-term variability, a count representative of the elapsed time between each heartbeat and the previous one is stored in a digital register and compared with the contents of an up-down counter (or its equivalent) which has stored in it a digital representation of the previous time difference, i.e. the elapsed time between the previous heartbeat and the one next preceding it. If the two stored values differ, incrementing or decrementing signals are applied to the up-down counter containing the previously stored beat-to-beat time difference value as necessary, until the numerical representation in the up-down counter is equal to the new value stored in the register. A comparison is made between the beat-to-beat time value stored in the register and the previous time value stored in the up-down counter and a determination of the greater and lesser of the two values is made. If the new time difference value stored in the register is greater than the representation in the up-down counter incrementing signals are applied to the up-down counter. When the stored new time difference value is less than the representation in the up-down counter, decrementing signals are applied to the up-down counter. Incrementing and decrementing signals are terminated when equality between the values in the register and up-down counter is reached. A cumulative absolute count of the number of increments or decrements necessary to achieve equality between the contents of the register and up-down counter is made and maintained by an accumulator or the like. After the predetermined number of heartbeats defining the measuring interval have occurred, the total absolute count is divided by the predetermined number of heartbeats to yield an average of the absolute values of the time differences between the successive heartbeats during the interval. This average is a numerical measure of short-term rate variability.

It is therefore an object of the invention to provide a method and apparatus for measuring long-term and short-term heart rate variability.

Another object of the invention is to determine the maximum and minimum heart rates of a subject in a predetermined heartbeat interval.

Still another object of the invention is to determine the average of the absolute differences in time between successive heartbeats in a predetermined measuring time interval.

A further object of the invention is to provide an alert signal when either short-term or long-term variability falls below a predetermined tolerance limit.

Other and further objects of the invention will be apparent from the following drawings and description of a preferred embodiment in which like-reference symbols are used to designate like parts in the various views.

DESCRIPTION OF THE DRAWINGS

FIG. 1 is a plot of heart rate vs. time showing heart rate variability;

FIGS. 2 through 6 are portions of an electrical schematic of the apparatus of the invention; and FIG. 7 is a block representation of the relationship between FIGS. 2 through 6.

DESCRIPTION OF THE PREFERRED EMBODIMENT

Figure 3:
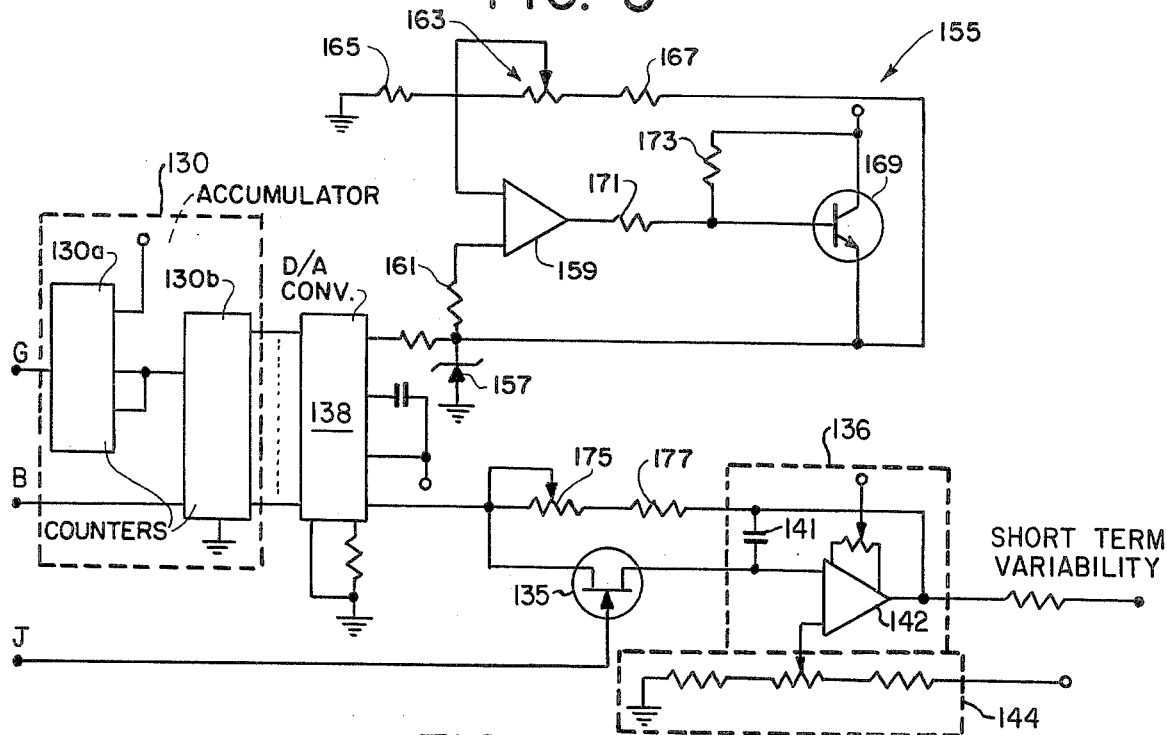

In the preferred embodiment of the invention electrical signals indicative of a subject's heart rate are applied to the inputs of the heart rate variability measurement system. The input signals may be obtained from a heart rate monitor of the type disclosed in U.S. Pat. No. 3,599,628 to Abbenante for FETAL HEART RATE AND INTRA-UTERINE PRESSURE MONITOR SYSTEM. In the monitor disclosed by Abbenante, heart rate data is available both in analog and digital form.

As can be seen in FIG. 1, from the plot of heart rate versus time, variability has both a long term and short term characteristic, the long term characteristic being represented by the envelope E of the curve and the short term characteristic being shown by the ripple R about the envelope E.

Long-term variability is determined from an analog heart rate input while short-term variability is computed from digital data indicative of the elapsed time between successive heartbeats, that is the beat-to-beat time difference, in the preferred embodiment of the invention. Digital and analog signals proportional to heart rate or beat-to-beat time difference, may be converted from one to another by techniques known to those familiar with the art and the invention may be practiced on either digital or analog data with respect to determination of either long-term or short-term variability. Furthermore short term, like long term, variability may be measured either in beats per unit time or time between heartbeats.

It has been found, however, that by measuring short-term variability in time units (milliseconds) rather than heart rate units (beats per minute) greater resolution may be achieved. This is so since time between heartbeats is the reciprocal of heart rate and the range of possible values of short-term variability measured in beat-to-beat time differences is greater than the corresponding reciprocal range of beats per minute.

Referring now to FIG. 2, an analog voltage proportional to a subject's instantaneous heart rate is applied to an input of the variability measurement system in electrical contact with node 2. The analog heart rate voltage is impressed across a differentiator circuit 1 which includes a capacitor 4 and an amplifier 6 and resistors 313 and 315. Long-term variability is computed from this analog input voltage. The differentiator circuit 1 serves as a high-pass filter eliminating extraneous and spurious low-frequency signals.

The output of the differentiator circuit 1 is applied through a resistor 305, to the source of a field effect transistor 8 which is controlled by the output of a transistor 10. The gate input of field effect transistor 8 is biased via resistors 307 and 311 and diode 309. The base of the transistor 10 is connected through a resistor 301 to a multivibrator or flip-flop circuit 12 (FIG. 4) having an input 13 to which inverted outputs of negative logic OR gate 14 (which is operatively equivalent to a NAND gate) connected to error check circuitry external to the variability measurement system are applied. The base and emitter of transistor 10 are coupled by resistor 303. Thus, for example, the error check circuitry may be programmed to generate an erroneous data signal and apply it to an input 11 in the variability measurement system when the measured heart rate appears to be less than thirty beats per minute. The external heart rate monitor may also generate a pen-lift signal when heart rate data is deemed improper, to prevent its chart recorder from recording the erroneous data. The pen-lift signal may be routed to an input 15 in the variability measurement system. These erroneous data signals are applied to the gate 14 through digital inverters 19 and 23 respectively and routed through an inverter 215 to the flip-flop 12 to control the transistor 10. One input of the gate 14 can receive a manually applied signal for testing the error check circuitry. The inverters 19 and 23 permit use of a NAND gate which herein performs the function of a negative logic OR gate.

When heart rate data is proper, the transistor 10 is biased closed, thereby causing the field effect transistor 8 to conduct. This permits the instantaneous analog heart rate voltage to be stored in a sample-and-hold circuit 16 which comprises a capacitor 18 and amplifier 20 and resistors 317 and 319. The capacitor 18 is charged to the input voltage which is proportional to the instantaneous sampled heart rate. The circuit 16 normally acts as an integrator to smooth the signal applied to it and serves as a sample and hold circuit to store the last valid signal when erroneous signals are detected until reception of proper signals resumes.

The output of the sample-and-hold circuit 16 is applied through a resistor 325 to comparators 21 and 22 and directly to field effect transistors 24 and 26 directly and to the gate inputs through resistors 347 and 343, respectively. The inputs of comparators 21 and 22 are coupled by capacitors 327 and 329, respectively. The field effect transistors 24 and 26 act as gates for a sample-and-hold circuit 28 comprising capacitor 30 and amplifier 32 and a sample-and-hold circuit 34 comprising capacitor 36 and amplifier 38 respectively. In the capacitor 30 of sample-and-hold circuit 28 there is stored a voltage proportional to the maximum of the heart rates previously sampled in the sampling interval and in the sample-and-hold circuit 34 there is stored a voltage proportional to the minimum of the previously sampled heart rates in the sampling interval.

The output of the sample-and-hold circuit 28 is connected to one input of the comparator 21. Similarly, the output of the sample-and-hold circuit 34 is applied to one intput of the comparator 22. The other inputs of comparators 21 and 22 respectively are connected to the output of the sample-and-hold circuit 16 to receive the sampled heart rate voltage stored in capacitor 18.

The two-state comparator 21 provides one output voltage if the maximum previous heart rate voltage stored in the sample-and-hold circuit 28 is less than the currently sampled heart rate voltage and a second output voltage if the maximum heart rate voltage stored in the sample-and-hold circuit 28 is exceeded by the currently sampled heart rate voltage. If the maximum heart rate voltage stored in the sample-and-hold circuit 28 is exceeded by the sampled heart rate voltage, the sampled heart rate voltage is applied to the sample-and-hold circuit 28 and replaces the previously stored maximum heart rate voltage, becoming the new maximum. This is accomplished as follows.

An interrogate circuit 40 senses an interrogate pulse to determine the state of the comparator 21 which is connected to an input of the interrogate circuit 40 biased via resistor 321. If the output of the comparator 21 indicates that the sampled heart rate voltage exceeds the maximum heart rate voltage stored in the sample-and-hold circuit 28 is a one-shot monostable multivibrator 42 is actuated to discharge a capacitor 335 which is charged through resistor 337 to apply a short-duration rectangular pulse to the base of a transistor 44 through resistor 345. This pulse causes the emitter-collector circuit of the transistor 44 to close and the output at the collector to be applied through the diode 349 to the gate of the field effect transistor 24 thereby causing the field effect transistor 24 to conduct. With the field effect transistor 24 now conducting, the sampled heart rate voltage stored in capacitor 18 of the sample-and-hold circuit 16 is conducted to the sample-and-hold circuit 28 where the capacitor 30 charges to the sampled heart rate voltage. Following termination of the pulse from the one-shot monostable multivibrator 42 the transistor 44 is again open and the field effect transistor 24 opens, leaving capacitor 30 of the sample-and-hold circuit 28 charged to a voltage proportional to the new maximum heart rate, that is the new sampled heart rate.

A circuit similar to the previously described one checks the currently sampled heat rate voltage to determine if it is less than the minimum heart rate voltage stored in the sample-and-hold circuit 34. The comparator 22 compares the currently sampled heart rate voltage with the minimum heart rate voltage stored in the capacitor 36 of the sample-and-hold circuit 34. If the sampled heart rate voltage is less than the heart rate voltage stored in the sample-and-hold circuit 34 an interrogate circuit 46, upon detecting the output of the comparator 22, actuates a one-shot monostable multivibrator 48, discharging a capacitor 339 charged through a resistor 341, the output of which is a rectangular pulse supplied to the base of a transistor 50 through resistor 346. This causes the normally open collector-emitter circuit of the transistor 50 to close and the output at the collector to be applied through diode 351 to the gate of the field effect transistor 26 thereby causing the field effect transistor 26 to conduct. Bias is provided to the gates of field effect transistors 24 and 26 via resistors 353 and 355, respectively. Transistors 44 and 50 are biased through resistors 357 and 359, respectively. The sampled heart rate voltage stored in the sample-and-hold circuit 16 is then applied to the sample-and-hold circuit 34 through the field effect transistor 26. At the termination of the rectangular pulse from the one-shot monostable multivibrator 48 the transistor 50 again opens, thereby opening the field effect transistor 26 and isolating the sample-and-hold circuit 34 from the heart rate voltage sampling circuitry.

When the sampled heart rate voltage does not exceed the heart rate maximum voltage for a previous sample stored in the sample-and-hold circuit 28, the interrogate circuit 40 upon sensing the output of the comparator 21 does not actuate the one-shot monostable multivibrator 42. As such, the transistor 44 remains in its normal open state leaving the field effect transistor 24 open so that the maximum heart rate voltage value stored in the sample-and-hold circuit 28 is not replaced by the currently sampled heart rate voltage. Similarly, when the sampled heart rate voltage is not less than the minimum previously sampled heart rate voltage stored in the sample-and-hold circuit 34 the interrogate circuit 46 upon sensing the output of the comparator 22 which is biased via resistor 323 does not actuate the one-shot monostable multivibrator 48. Therefore, the transistor 50 remains in its normal open state and the field effect transistor 26 is held open thereby preventing the minimum heart rate voltage stored in the sample-and-hold circuit 34 from being replaced by the currently sampled heart rate voltage.

The outputs of the sample-and-hold circuits 28 and 34 containing the respective previously sampled maximum and minimum heart rate voltages are applied to respective inputs of a differential amplifier 52 through resistors 361 and 363. The output of the differential amplifier 52 which is fed back to the minimum heart rate voltage input through resistor 365 and applied to the gate of a field effect transistor 60 through resistor 367 is a voltage proportional to the difference between the maximum and minimum heart rate voltages for the time interval during which the maximum and minimum heart rate voltages stored in respective sample-and-hold circuits 28 and 34 have been updated. The maximum heart rate voltage input of differential amplifier 52 is biased via voltage divider resistors 369 and 371.

Figure 4:
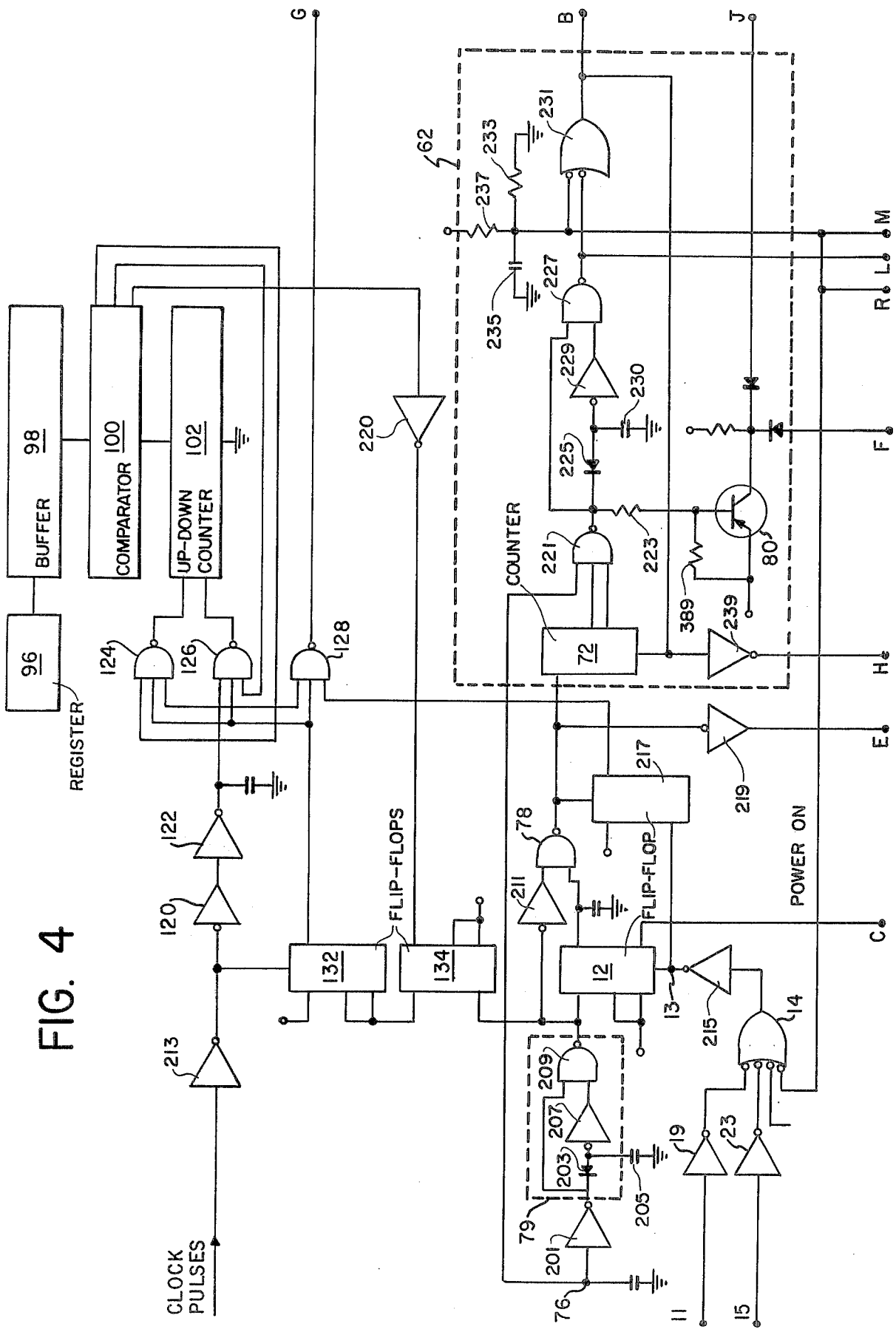

The difference voltage output of the amplifier 52 is applied to the input of a sample-and-hold circuit 54 comprising a capacitor 56 and an amplifier 58. Disposed between the output of the differential amplifier 52 and input of the sample-and-hold circuit 54 is a field effect transistor 60 which is controlled by a counting circuit 62 (FIG. 4). The counting circuit 62 counts successive heartbeats for each time interval in which long-term and short-term heart rate variability is to be computed.

In the preferred embodiment of the invention the measuring time interval is set at 512 heartbeats. The counting is accomplished in binary counter 72 which is actuated in response to detection of an incrementing pulse generated by a pulse forming network 79 when the leading edge of a heartbeat transfer signal at node 76, which is produced by the external heart monitor in reponse to each heartbeat, is detected. The pulse forming network 79 receives its input from the output of an inverter 201 which includes a diode 203 connected to a grounded capacitor 205 and the input of an inverter 207, the outputs of the inverters 201 and 207 being connected to respective inputs of a NAND gate 209. The output of the pulse forming network 79 is taken from the output of the NAND gate 209. Provision is made for applying an a.c. test signal to node 76 at a frequency substantially greater than that of the heart rate to simulate a very rapid transfer signal. This enables the system to be tested for proper operation with virtually no delay.

The incrementing signal is applied through an inverter 211 and a gate 78 to the counter circuit 62 wherein the count in the binary counter is incremented once for each heartbeat. The output signals from the gate 78 are also applied to the gates 40 and 46 through an inverter 219 for interrogating comparators 21 and 22, respectively. In the event that received heart rate data is deemed improper by the external editor circuitry as previously described, flip-flop multivibrator circuit 12 causes the gate 78 to close thereby preventing the count in the counter circuit 62 from being incremented in response to the erroneous heart rate signal.

When the preselected number of heartbeats defining the measuring time interval is reached the counter 72 enables a NAND gate 221 and a signal voltage is applied in the counter circuit 62 through a resistor 223 to the base of a transistor 80 the emitter of which is coupled to the base through resistor 389 and is biased at a positive five volts to normally keep the transistor turned off. This signal voltage causes the emitter-collector circuit of the transistor 80 to close and, hence, the field effect transistors 60 (FIG. 2) and 135 (FIG. 3) to conduct so that the output of the differential amplifier 52 is applied to the input of the sample-and-hold circuit 54 causing the capacitor 56 to charge to a voltage proportional to the difference between the maximum and minimum heart rates in the measuring interval. The output of the NAND gate 221 can also be applied directly to one input of a NAND gate 227 and through a diode 225 and inverter 229 to the other input of the NAND gate 227 for clearing the counter 72 and an accumulator 130 the function of which will later be described. The input of the inverter 229 is connected to a grounded capacitor 230. A pulse forming network for generating a pulse for clearing of the counter 72 and accumulator 130 in response to the trailing edge of the output signal from gate 221 comprises diode 225, inverter 229, capacitor 230 and gate 227. The clearing signal from NAND gate 227 is applied to the counter 72 and accumulator 130 through a negative OR gate 231 where the output signal from the NAND gate 227 is inverted. The output of the gate 231 is also applied through an inverter 239 to multivibrators 42 and 48 to trigger the multivibrators 42 and 48 for resetting sample and hold circuits 28 and 34 for a new variability computation. To initialize the system when the power is turned on, the gate 231 has another input for receiving a counter clearing signal from a power reset network comprising a grounded parallel RC circuit including a resistor 233 and capacitor 235 to which a direct voltage can be applied through a resistor 237.

The output of the sample-and-hold circuit 54 is a voltage having a magnitude which is a quantitative measurement of long-term variability for the measuring time interval. This analog voltage may be applied directly to a chart recorder or other display and to an alert circuit as well.

Figure 5:
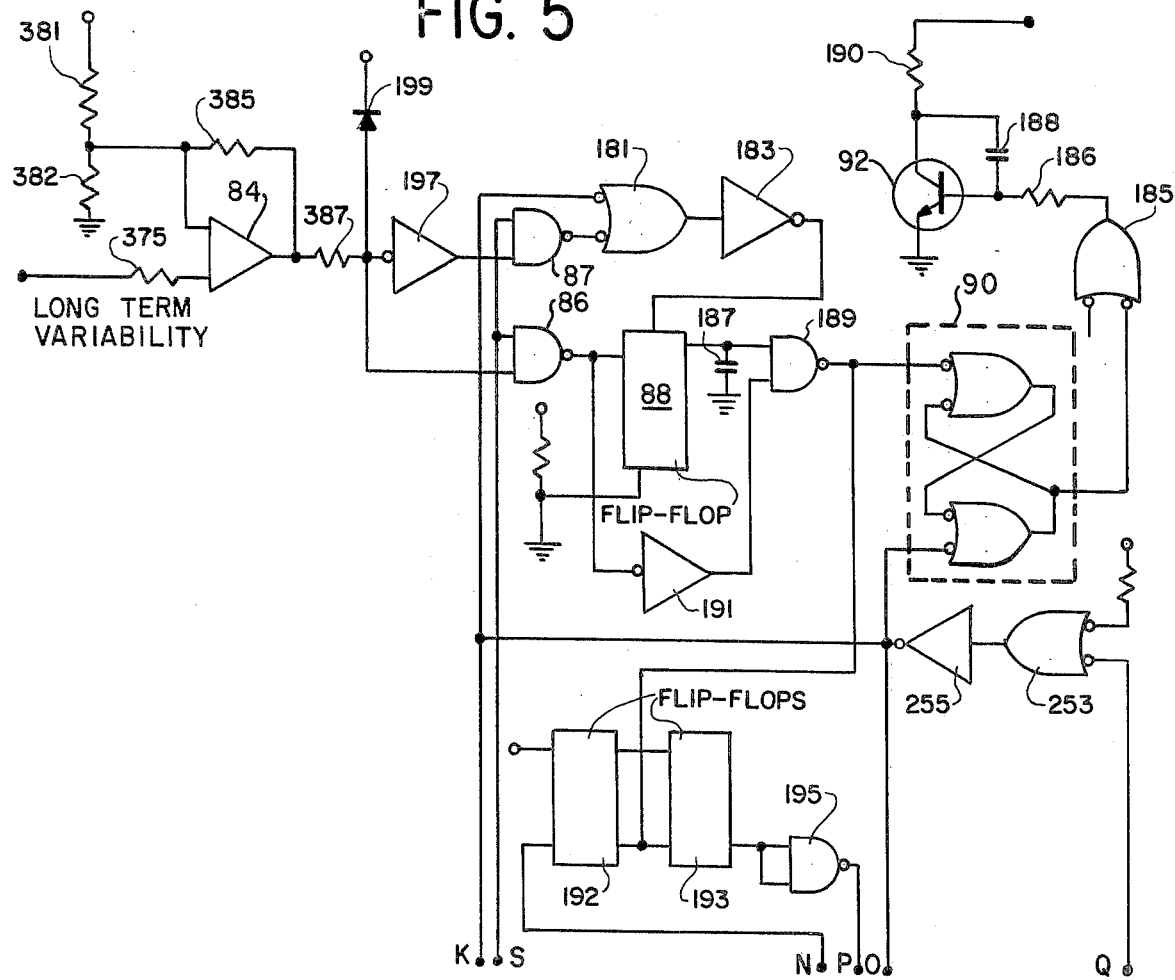

A long-term variability alert circuit (FIG. 5) comprises a comparator 84 which has applied to one of its inputs a voltage proportional to a variability tolerance limit which when not exceeded by the output voltage of the sample-and-hold circuit 54 provides an indication of poor variability to be used for alerting medical personnel to the existence of the abnormal heart rate variability condition. Applied to the other input of the comparator 84 through resistors 373 and 375 is the output voltage of the sample-and-hold circuit 54. Interrogate circuits 86 and 87 sense pulses from the output of gate 227 at the end of each measuring interval to interrogate the state of the output of the comparator 84 which is a voltage fed back through resistor 385 and applied to inverter 197 through resistor 387 to determine if an unacceptable variability condition exists. The output pulses from gate 227 are applied to gates 86 and 87 through inverter 241, NAND gate 243 and inverter 245. Since the heart rate measuring electrode may not be properly positioned when first applied to a subject, a flip-flop 247 is actuated when power is first turned on for disabling interrogate pulses from passing through NAND gate 243 to prevent the variability during the first measuring interval from being counted in determining whether an alarm should be sounded. The flip-flop 247 is reset at the end of the first measuring interval to permit the interrogate pulses to pass through gate 243. The flip-flop 247, when set in response to the system being turned on, actuates a transistor 251 the collector of which is connected to one input of a negative OR gate 253 (FIG. 5) for causing a reset signal to appear at the output of the gate 253. The other input of the gate 253 is connected to a voltage source to provide a reset signal at the output of the gate 253 whenever the variability measurement system is turned off. The output of the gate 253 is applied through an inverter 255 to gate 181 for resetting counter 88, to one input of a negative OR gate 261 the output of which is connected to an inverter 263 for resetting flip-flops 191 and 193, and to a negative OR gate 265 the output of which is connected to an inverter 267 for resetting flip-flops 269 and 271. Flip-flops 269 and 271 are operatively connected to inverting gate 273 for preventing resumption of an insufficient short-term variability indication after the variability indicator is reset unless a period of sufficient short-term variability first occurs. The other input of the gate 261 is connected to receive the power reset signal from RC network 233, 235 for resetting flip-flops 191 and 193 when the power is turned on. The gate 86 is biased directly through diode 199 while the bias to gate 87 is applied through an inverter 197. A variability tolerance voltage is applied to comparator 84 via voltage divider resistors 381 and 382. Instead of alerting each time the variability tolerance is not exceeded in a measuring time interval, it is desirable, in order to avoid false alarms, to actuate the alarm only after a poor variability condition exists for a consecutive number of measuring time intervals.

A binary counter 88 is employed which is incremented at the end of each measuring time interval in which variability fails to exceed the prescribed tolerance. The counter 88 is reset to zero by an output signal from an inverter 183 that receives at its input the output of the negative OR gate 181, which has one input connected to the output of the interrogate circuit 87, whenever a time interval is completed in which the long-term variability measurement exceeds the tolerance level. The counter 88 is provided with means, known to those familiar with the art for indicating when a predetermined count is reached. Where an alarm is to be sounded after two consecutive measuring intervals of unacceptable variability, counter 88 can be a flip-flop having an output connected to a grounded capacitor 187 and one input of a NAND gate 189. To the other input of the gate 189 there is connected the output of an inverter 191 which, in turn, has applied to its input the output of the gate 86. In this case the multivibrator 90 is actuated by the output of gate 189 only after two consecutive intervals of insufficient variability. Interrogate circuit 86 determines whether the variability tolerance voltage has not been exceeded and, if this is the case, applies an incrementing signal to the counter 88. Interrogate circuit 87 determines whether the variability tolerance voltage has been exceeded and, if so, applies a clearing signal to the counter 88 to reset it to zero as described above.

When the count in the binary counter 88 reaches the preselected number of measuring intervals for the sounding of an alert, a signal is sent to a multivibrator circuit 90 which switches to actuate an audio and visual alarm. The output of the multivibrator 90 is applied to the transistor 92 through one input of a negative OR gate 185. The OR gate has another input to which a signal may be applied for testing the variability lamps. The output of the gate 185 is connected to a resistor 186 which limits the current applied to the base of the transistor 92. A capacitor 188 connected between the base and collector of transistor 92 prevents current surges. The output of the transistor 92 is applied to the variability warning lamp through a current limiting resistor 190. A transistor 92 drives a signal light to indicate the existence of an alert condition. Additional circuitry known to those familiar in the art causes the sounding of an audio signal to indicate the existence of abnormal heart rate variability.

For the determination of short-term variability in the preselected measuring time interval, the value of the time elapsed since the last previous heartbeat represented in digital form in the external heart rate monitor, as for example in one of the type disclosed in Abbenante, is sampled with the occurrence of each heartbeat of the subject. The sampled beat-to-beat time interval is stored in digital form in a resistor 96 (FIG. 4) which may be the one included in the external heart rate monitor. Connected to the register 96 is a buffer 98 which receives the digital beat-to-beat time data from the register 96. A comparator circuit 100 is connected to the buffer circuit 98 and to an up-down counter 102. Initially, the first beat-to-beat time interval sampled in the selected measuring time interval and stored in the register 96 is also stored in the up-down counter 102. Each time a new heart rate value is sampled it is stored in the register 96 replacing the value previously stored in it. The contents of the register 96 are then compared in the comparator 100 with those of the up-down counter 102. If they are unequal, the up-down counter is incremented or decremented, as required until equality between the numerical representation in the register 96 and up-down counter 102 respectively is attained.

An external clock circuit (not shown), as for example employing an oscillator known to the art, supplies pulses to the up-down counter 102 to increment or decrement it as required. Logic gates 124 and 126 are connected to the comparator 100 and receive signals indicative of whether the count in the buffer 98 from the register 96 is greater than, equal to, or less than the count in the up-down counter 102. Gate 124 is connected to a decrementing input of the up-down counter 102 and gate 126 is connected to an incrementing input of the up-down counter 102. When the count in the up-down counter is the greater one, gate 124 admits pulses from the block to the decrementing input of the up-down counter which causes its count to be decremented. At this time gate 126 admits no pulses to the incrementing input. When the count in the buffer 98 is the greater one the opposite occurs. That is, gate 126 admits clock pulses to the incrementing input of the up-down counter 102 while gate 124 prevents clock pulses from reaching the decrementing input of the up-down counter 102. Inverter circuits 120 and 122 delay the pulses from the external clock oscillator applied through inverter 213 and keep them from reaching the up-down counter 102 until after the new data can be evaluated. If the new data, that is the next beat-to-beat time difference, is erroneous the editor circuitry has time to interrupt the path to the up-down counter 102 so that the erroneous data does not affect the variability measurement. The time delayed pulses are applied to the up-down counter via the gates 124 and 126. At the same time the clock pulses which increment or decrement the up-down counter 102 are applied via a gate 128 to an accumulator 130 (FIG. 3) which keeps a count of the number of pulses required to bring the contents of the up-down counter 102 into equality with the contents of the register 96. The accumulator 130 comprises two smaller capacity counters 130a and 130b connected together to operate as a single higher capacity counter in a manner known to those familar with the art.

In the event that received heart rate data is deemed erroneous according to the external editor circuitry, the gate 128 is closed in response to the erroneous data signal thereby preventing the erroneous heart rate signal from influencing the count in the accumulator 130. Flip-flop 217 prevents the accumulator 130 from continuing its count following an erroneous data signal until the second acceptable heart rate input signal is received. A synchronizer (flip-flop) circuit 132 synchronizes the transfer pulses generated in response to each heartbeat with the oscillator clock incrementing and decrementing pulses. Only complete clock pulses and not partial pulses are permitted to affect the up-down counter 102 and accumulator 130. Thus if a clock pulse occurs during a transfer (heartbeat) pulse, that clock pulse is blocked by the synchronizer 132. A flip-flop 134 is set in response to the output of NAND gate 209 with each transfer pulse. Each time the count in the up-down counter 102 equals the count in the buffer 98 an output of the comparator 100, inverted in inverter 220, resets the flip-flop 134. The flip-flop 134 enables the flip-flop 132 to be set and reset in synchronization with the clock pulses.

The transfer pulses permit data to enter the system. Following each erroneous data signal from the external monitor, the enable flip-flop circuit 12 prevents incrementing and decrementing pulses from the external clock from updating the count in the accumulator 130 until data from two successive heartbeats indicative of valid heart rates is received. This insures that any adverse condition resulting in erroneous heart rate data is no longer present.

The 12-bit accumulator 130 in addition to receiving incrementing and decrementing pulses from the external clock is also connected to the heartbeat counter circuit 62. The output signal of the counter 62 which indicates that the preselected number of heartbeats in the measuring time interval, i.e., 500 heartbeats, has occurred is applied to the accumulator 130 to clear it for a new count. However, before the accumulator is cleared, its count is stored in a sample and hold circuit 136. This is accomplished via field effect transistor 135 which is rendered conductive by the closing of the collector-emitter circuit of transistor 80 in a manner similar to the storage of the long-term variability voltage in the sample and hold circuit 54 via the field effect transistor 60 which is also controlled by transistor 80. As previously described, an output signal from the counter circuit 62 is applied to the base of the transistor 80 causing it to close, thereby rendering the field effect transistor 135 conductive. This causes the count in the accumulator 130 which is converted to an analog-voltage via a digital to analog converter 138 to be stored in a capacitor 141 of the sample-and-hold circuit 136. A voltage regulator circuit 155 provides a stable voltage reference for the digital to analog converter 138. The regulator circuit 155 includes a zener diode 157 connected to one input of an amplifier 159 through a resistor 161. The other input of the amplifier 159 is connected to the wiper of a potentiometer 163. The winding of the potentiometer 163 is connected at one end to a grounded resistor 165 and at its other end to a resistor 167 which is, in turn, connected to the emitter of a transistor 169 and the zener diode 157. The output of the amplifier 159 is applied to the base of the transistor 169 through a resistor 171. The base and collector of the transistor 169 are tied together via a resistor 173.

Also incorporated in the 12-bit accumulator 130 is provision for applying a correction factor to the count stored in the accumulator whereby that count is divided by the number of heartbeats in the measuring interval, that is, 512, to yield the average of the absolute values of the differences in times between successive heartbeats. A further correction is applied by the accumulator to compensate for the fact that time differences are measured in units of 1.953 milliseconds for convenience in selecting hardware for the practice of the invention. A correction factor is necessary to convert the time measuring unit to milliseconds. The corrections may also be made via a level shift circuit 144 as well as by suitable selection of the gain of amplifier 142 in the sample and hold circuit 136.

As stated above, the digital to analog converter 138 is disposed between the accumulator 130 and the field effect transistor 135 to convert the digital data stored in the accumulator into analog form. The data in analog form is applied to the sample-and-hold circuit 136 comprising the capacitor 141 and amplifier 142 when the field effect transistor 135 is turned on in response to the closing of the emitter-collector circuit in the transistor 80. Gain control is effected by variable resistor 175 and resistor 177. The output of the sample-and-hold circuit 136 is a voltage which is proportional to short-term heart rate variability expressed in milliseconds between successive beat-to-beat intervals. The level shift circuit 144 is provided at one of the inputs to the amplifier 142 to scale the voltage in the sample-and-hold circuit 136 for compatibility with a recorder by which the short-term variability data is to be plotted as well as to apply necessary correction factors as hereinbefore discussed.

Figure 6:
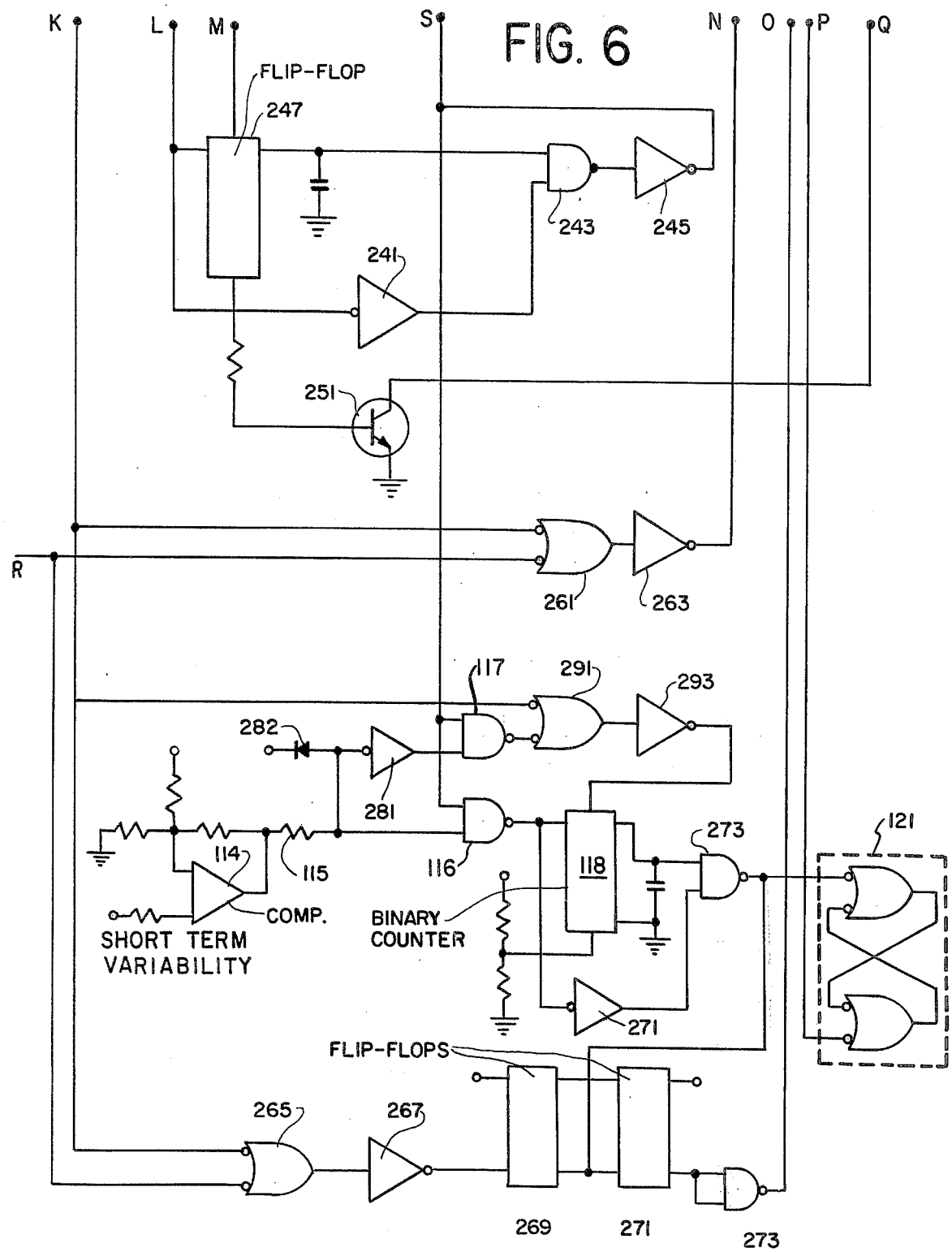

The variability measurement system is also provided with a short-term variability alert circuit (FIG. 6). The short-term variability alert circuit comprises a comparator 114 with two inputs. To one input there is applied the analog output voltage of the sample-and-hold circuit 136 indicative of short-term variability and to the other input there is applied a voltage proportional to a minimum tolerance level for short-term variability. Interrogate circuits 116 and 117 receive the same interrogate pulses as do gates 86 and 87 to determine the state of the comparator 114 which has its output connected through resistor 115 to gate 116 and additionally through an inverter 281 to gate 117. Diode 282 limits the voltage applied to the input of inverter 281. When the short-term variability voltage tolerance is not exceeded by the output voltage of the sample-and-hold circuit 136d which is proportional to short-term heart rate variability a binary counter 118 is incremented by the output of gate 116. The counter 118 can be a flip-flop which operates in conjunction with inverter 271 and NAND gate 273 to count to two. Each time a measuring time interval is completed in which the short-term variability voltage in the sample-and-hold circuit 136 exceeds the tolerance level voltage applied to the comparator 114 the counter 118 is reset to zero by the output of gate 117 which is applied to a negative OR gate 291 and then through an inverter 293 to a reset input of the counter 118. When a predetermined number of consecutive sampling intervals in which the threshold short-term variability level is transcended is reached, a multivibrator circuit 121 is actuated causing the visual and audio alert alarms to be actuated in a manner similar to that heretofore described in conjunction with the discussion of the long-term variability alert. When the variability alarm is reset after sounding, flip-flops 192 and 193 and inverting gate 195 prevent the alarm from again actuating until a measuring interval of sufficient variability first occurs.

It will be noted that the above description is of a preferred embodiment of the invention which may be practiced by other configurations of the circuitry disclosed which will be known to those familiar with the art upon reading this specification without departing from the spirit of the invention and that the scope of the invention is to be limited only by the following claims.

What is claimed is:

1. Apparatus for measuring heart rate variability comprising
   means for receiving periodic voltage signals each having a characteristic with a magnitude proportional to a subject's heart rate,
   means for storing a first voltage having a characteristic with a magnitude proportional to the previous maximum heart rate of the subject,
   means for storing a second voltage having a characteristic with a magnitude proportional to the previous minimum heart rate of the subject,
   first means for comparing the magnitude of said characteristic of said received voltage with the magnitude of said characteristic of said first voltage,
   means responsive to said first comparing means for storing said received voltage in said first voltage storing means only when the magnitude of said characteristic of said received voltage exceeds the magnitude of said characteristic of said stored first voltage,
   second means for comparing the magnitude of said characteristic of said received voltage with the magnitude of said characteristic of said second voltage,
   means responsive to said second comparing means for storing said received voltage in said second voltage storing means only when the magnitude of said characteristic of said received voltage is less than the magnitude of said characteristic of said second voltage, and
   means for determining the difference between the magnitudes of said characteristics of said first and second voltages respectively.

2. Apparatus according to claim 1 further comprising
   timing means for counting a first predetermined number of occurrences of a recurring event, the count in said timing means being reset to zero and said first and second voltages being cleared from said means for storing said first and second voltages respectively after said predetermined number is reached.

3. Apparatus according to claim 2 wherein said recurring event is the heartbeat of said subject.

4. Apparatus according to claim 2 further comprising means for storing a predetermined tolerance voltage having a characteristic with a magnitude proportional to a predetermined minimum permissible measure of variability,
   third means for comparing said voltage characteristic magnitude difference with the magnitude of said characteristic of said tolerance voltage each time said first predetermined number is reached by said timing means, counting means responsive to said third comparing means for counting the number of consecutive times said tolerance voltage characteristic magnitude is not exceeded, the count in said counting means being reset to zero each time said first predetermined number is reached with said threshold voltage characteristic magnitude exceeded by said voltage characteristic magnitude difference, and means responsive to said counting means for generating a signal indicative of unsatisfactory variability each time said count exceeds a second predetermined number.

5. Apparatus for measuring heart rate variability comprising means for storing a first count indicative of the most recent measured beat-to-beat time between successive heartbeats of a subject, means for storing a second count indicative of a previous measured beat-to-beat time of the subject, first means for comparing said first and second counts, means responsive to said comparing means for providing sequential signals to said second storage means for increasing the count in said second storage means when said first count is greater than said second count until said second count is equal to said first count, second means responsive to said comparing means for providing sequential signals to said second storage means for decreasing the count in said second storage means when said first count is less than second count until said second count is equal to said first count, and means responsive to said first and second sequential signal means for cumulatively counting the number of signals required to equalize the counts in said means for storing said first and second counts respectively.

6. Apparatus according to claim 5 further comprising timing means for counting a first predetermined number of occurrences of a recurring event after which the counts in said timing means and in said cumulative counting means are reset to zero to begin a new variability measuring time interval.

7. Apparatus according to claim 6 wherein said recurring event is the heartbeat of said subject.

8. Apparatus according to claim 6 further comprising means for storing at tolerance count having a magnitude proportional to a predetermined minimum permissible measure of heart rate variability, second means for comparing the value of said cumulative count with that of said stored tolerance count each time said first predetermined number is reached, additional counting means responsive to said second comparing-means for counting the number of consecutive times said tolerance count is not exceeded, the count in said additional counting means being reset to zero each time said first predetermined number is reached with said tolerance count exceeded, and means responsive to said additional counting means for generating a signal indicative of unsatisfactory variability each time said count exceeds a second predetermined number.

9. A method of measuring heart rate variability comprising a. periodically receiving voltage signals each having a characteristic with a magnitude proportional to the subject's heart rate, b. storing a first voltage having a characteristic with a magnitude equal to that of the first received voltage signal, said first voltage to be maintained with the magnitude of its characteristic proportional to the maximum heart rate of the subject, c. storing a second voltage having a characteristic with a magnitude equal to that of the first received voltage signal, said second voltage to be maintained with the magnitude of its characteristic proportional to the previous minimum heart rate of the subject, d. comparing the magnitude of a characteristic of each subsequent received voltage signal with the magnitude of said characteristic of said first voltage, e. equalizing the magnitude of said characteristic of said first voltage with that of said received voltage only when the magnitude of said characteristic of said received voltage exceeds the magnitude of said characteristic of said first voltage, f. comparing the magnitude of said characteristic of said received voltage with the magnitude of said characteristic of said second voltage, g. equalizing the magnitude of said characteristic of said second voltage with that of said received voltage only when the magnitude of said characteristic of said received voltage is less than the magnitude of said characteristic of said second voltage, and h. determining the difference between the magnitude of said characteristics of said first and second voltages respectively.

10. A method according to claim 9 further comprising sequentially repeating steps (a), (d), (e), (f), and (g) after step (g) while counting a first predetermined number of occurrences of a recurring event, and only when said first predetermined number is reached, continuing to step (h).

11. A method according to claim 10 further comprising resetting said count to zero after step (h) is performed.

12. A method according to claim 11 wherein said recurring events are the subject's heartbeats.

13. A method according to claim 10 further comprising storing a predetermined tolerance voltage having a characteristic with a magnitude proportional to a predetermined minimum permissible measure of variability, comparing said voltage characteristic magnitude difference with the magnitude of the characteristic of said tolerance voltage each time said first predetermined number is reached, counting the number of consecutive times said tolerance voltage characteristic magnitude is not exceeded, and generating an alert signal each time said consecutive count exceeds a second predetermined number.

14. A method of measuring heart rate variability comprising storing a first count indicative of the most recent measured heart beat-to-beat time between successive heartbeats of a subject, storing a second count indicative of a previous measured beat-to-beat time of the subject, comparing said first and second counts, providing sequential signals for increasing said second count when said first count is greater than said second count until said second count is equal to said first count, providing sequential signals count for decreasing said second when said first count is less than said second count until second count is equal to said first count, and cumulatively counting the number of signals required to equalize said first and second counts.

15. A method according to claim 14 further comprising storing a tolerance count having a magnitude proportional to a predetermined minimum permissible measure of variability, comparing said cumulative count with the magnitude of said tolerance count each time said predetermined count is reached, counting the number of consecutive times said tolerance count is not exceeded, and generating an alert signal each time said consecutive count exceeds a predetermined value.

* * * * *

UNITED STATES PATENT OFFICE
CERTIFICATE OF CORRECTION

Patent No. 4,018,219    Dated   April 19, 1977

Inventor(s)   George Hojaiban

It is certified that error appears in the above-identified patent and that said Letters Patent are hereby corrected as shown below:

In claim 5, column 13, line 33, after "than" insert --said--;

In claim 8, column 13, line 50, change "at" to --a--;

In claim 14, column 15, line 5, after "signals" delete --count--;

line 6, after "second" insert --count--;

line 7, after "until" insert --said--.

Signed and Sealed this

Ninth Day of May 1978

[SEAL]

Attest:

RUTH C. MASON
Attesting Officer

LUTRELLE F. PARKER
Acting Commissioner of Patents and Trademarks